United States Patent
Sada et al.

[11] Patent Number: 6,028,081
[45] Date of Patent: Feb. 22, 2000

[54] SUBSTITUTED QUINOLONE DERIVATIVES AND PHARMACEUTICALS CONTAINING THE SAME

[75] Inventors: Yoshihisa Sada; Shigeru Adegawa; Kinichi Mogi, all of Narita; Haruyoshi Honda, Tomisato-machi; Hiromichi Eto, Narita; Shinichi Morimoto, Sakura; Junji Okawa, Tomisato-machi; Norimitsu Umehara, Tokorozawa; Susumu Sato, Narita, all of Japan

[73] Assignee: SSP Co., Ltd., Tokyo, Japan

[21] Appl. No.: 09/141,374

[22] Filed: Aug. 27, 1998

[30] Foreign Application Priority Data

Aug. 29, 1997 [JP] Japan ..................... 9-234547

[51] Int. Cl.$^7$ .......... A61K 31/47; A61K 31/55; C07D 501/12; C07D 215/16
[52] U.S. Cl. .......... 514/312; 514/220; 546/156; 546/157; 546/158; 540/495
[58] Field of Search ..................... 546/156, 157, 546/158; 514/312, 220; 540/495

[56] References Cited

U.S. PATENT DOCUMENTS 5,412,104  5/1995  Afonso ..................... 548/525

OTHER PUBLICATIONS

Chemical abstracts 119:72518, Fiala, 1993.
Chemical Abstracts 107:134174, Stadlbauer, 1986.
Chemical Abstracts 60:2915f, Robinson.

*Primary Examiner*—D. Margaret Seaman
*Attorney, Agent, or Firm*—Oblon, Spivak, McClelland, Maier & Neustadt, P.C.

[57] ABSTRACT

Substituted quinolone derivatives represented by the following formula:

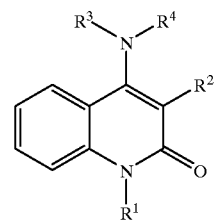

wherein $R^1$ represents a substituted or unsubstituted (hetero) aryl group, $R^2$ represents H or an alkoxycarbonyl, substituted aminocarbonyl, cyano or like group, and $R^3$ and $R^4$ each independently represent H or a substituted alkyl, aryl, amino or like group, and salts thereof; pharmaceuticals containing the same. These derivatives and salts have excellent anti-ulcer activities.

5 Claims, No Drawings

SUBSTITUTED QUINOLONE DERIVATIVES AND PHARMACEUTICALS CONTAINING THE SAME

BACKGROUND OF THE INVENTION a) Field of the Invention

This invention relates to substituted quinolone derivatives or salts thereof excellent in therapeutic effects for peptic ulcer and also to pharmaceuticals containing the same.

b) Description of the Related Art

In today's stressful society, diseases of the digestive system, especially peptic ulcers, have tended to increase and have become a problem. Antiulceratives can be roughly divided into two types, one being the gastric acid secretion inhibition type and the other the defensive factor potentiating type. The former includes H2-blockers led by cimetidine, proton-pump inhibitors represented by omeprazole, and the like, and from the viewpoint of "no acid, no ulcer" (there is no ulcer where no acid exists), features strong inhibition of secretion of gastric acid as the means to cure ulcers. They are sharp-effecting and are used most widely clinically. On the other hand, the latter type make ulceration difficult by enhancing the self-healing ability and resistance of the gastric mucosa, and include gefarnate, teprenone, rebamipide, prostaglandin derivatives, and the like. They feature mild effects and relatively low side effects, and are used for the treatment of gastritis or gastric disorders caused by chemicals or as supplementary medicaments for antiulceratives of the gastric acid secretion inhibition type.

However, the conventional antiulceratives of the gastric acid secretion inhibition type are accompanied by problems such as rebounding of gastric acid secretion by termination of an administration and a recurrence or relapse of an ulcer due to a reduction in Q.O.U.H. (Quality of Ulcer Healing). On the other hand, the antiulceratives of the defensive factor potentiating type, while being of mild activity, are not sharp-effecting. There is accordingly a strong desire for the development of an antiulcerative which has stronger antiulcerative activity yet has low side effects such as rebounding and high safety.

SUMMARY OF THE INVENTION

An object of the present invention is therefore to provide a pharmaceutical having excellent antiulcerative effects and having low side effects and high safety.

In view of such circumstances, the present inventors have proceeded with extensive research. As a result, it has been found that novel substituted quinolone derivatives represented by the below-described formula (1) can solve the above-described problems and can be used as pharmaceuticals effective for the treatment of peptic ulcers and the like.

Namely, the present invention provides a substituted quinolone derivative represented by the following formula (1):

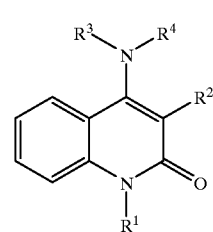

wherein $R^1$ represents a substituted or unsubstituted aryl or heteroaryl group, $R^2$ represents a hydrogen atom, a group $COOR^5$ in which $R^5$ represents a hydrogen atom or a substituted or unsubstituted alkyl, aralkyl or heteroaralkyl group, a group $CON(R^6)R^7$ in which $R^6$ and $R^7$ may be the same or different and each independently represent a hydrogen atom or a substituted or unsubstituted alkyl or aryl group, or a cyano group, $R^3$ and $R^4$ may be the same or different and each independently represent a hydrogen atom or a substituted or unsubstituted alkyl, aryl or amino group, or $R^3$ and $R^4$ are combined with the adjacent nitrogen atom to form a heterocycle or one of $R^3$ and $R^4$ and one of $R^6$ and $R^7$ are combined together to form a ring, or a salt thereof; and also a pharmaceutical comprising the derivative or salt as an active ingredient.

The substituted quinolone derivative (1) or its salt according to the present invention has excellent antiulcerative activity and therefore, is useful as an antiulcerative.

DETAILED DESCRIPTION OF THE INVENTION AND PREFERRED EMBODIMENTS

The substituted quinolone derivative or its salt according to the present invention is a novel compound represented by the above formula (1), and is different from conventional compounds containing the quinolone skeleton as a base structure and having antiulcerative activity, namely, the compounds disclosed in JP kokai 171975/1982, JP kokai 228076/1987, JP kokai 158281/1987, JP kokai 234389/1992, JP kokai 25170/1993, JP kokai 25171/1993 and JP kokai 25172/1993.

In the formula (1), the aryl group represented by $R^1$ can be a phenyl group, a naphthyl group or the like whereas the heteroaryl group represented by $R^1$ can be a 5- or 6-membered heteroaryl group containing 1–3 nitrogen atoms, for example, a pyridyl group, a pyrimidyl group or the like. These aryl or heteroaryl groups may each contain one or more substituent groups. Examples of the substituent groups can include linear or branched alkyl or alkoxyl groups having 1–6 carbon atoms, halogen atoms, and trihalogenomethyl groups. These aryl or heteroaryl groups may each be substituted preferably by one to five, especially one to three of these substituent groups. Here, examples of the linear alkyl groups having 1–6 carbon atoms can include methyl, ethyl, propyl, butyl, pentyl, and hexyl groups, and examples of the branched alkyl groups having 1–6 carbon atoms can include isopropyl, isobutyl and t-butyl groups. Illustrative of the linear alkoxyl groups having 1–6 carbon atoms can be methoxy, ethoxy, propoxy and hexyloxy groups, and illustrative of the branched alkoxyl groups having 1–6 carbon atoms can be isopropyloxy, isobutyloxy and t-butyloxy groups. Examples of the halogen atoms can include fluorine, chlorine, bromine and iodine atoms. Examples of the trihalogenomethyl groups can include trifluoromethyl, trichloromethyl and tribromomethyl groups. Among these, a phenyl group is particularly preferred as the group represented by $R^1$.

Further, the alkyl group represented by $R^5$ in the group COOR$^5$ among the groups, which may be represented by $R^2$ in the formula (1), can be a linear or branched alkyl group having 1–6 carbon atoms. Here, examples of the linear alkyl group having 1–6 carbon atoms can include methyl, ethyl, propyl, butyl, pentyl, and hexyl groups, and examples of the branched alkyl group having 1–6 carbon atoms can include isopropyl, isobutyl and t-butyl groups. Illustrative of the aralkyl group can be $C_6$–$C_{10}$aryl-$C_{1-6}$alkyl groups, for example, benzyl and phenethyl groups. Illustrative of the heteroaralkyl group can be pyridyl-$C_{1-6}$alkyl groups, for example, a pyridylmethyl group.

The alkyl group represented by $R^6$ and $R^7$ in the group CON($R^6$)$R^7$ can be a linear or branched alkyl group having 1–6 carbon atoms. Here, examples of the linear alkyl group having 1–6 carbon atoms can include methyl, ethyl, propyl, butyl, pentyl, and hexyl groups, and examples of the branched alkyl group having 1–6 carbon atoms can include isopropyl, isobutyl and t-butyl groups. These alkyl groups represented by $R^5$, $R^6$ and $R^7$ may each contain one or more substituent groups. Illustrative of the substituent groups can be hydroxyl groups, alkoxyl groups, halogen atoms, and substituted amino groups. The number of these substituent groups may preferably be from 1 to 3. Among these substituent groups, the alkoxyl groups can preferably be linear or branched alkoxyl groups having 1–6 carbon atoms. Illustrative of the linear alkoxyl groups having 1–6 carbon atoms can be methoxy, ethoxy, propoxy, and hexyloxy groups, and illustrative of the branched alkoxyl groups having 1–6 carbon atoms can be isopropyloxy, isobutyloxy and t-butyloxy groups. Illustrative of the halogen atoms can be fluorine, chlorine, bromine and iodine atoms. Further, examples of the amino groups substituted on the alkyl groups can include amino groups substituted by one or more linear or branched alkyl groups having 1–6 carbon atoms, and a phenylureido group. Here, illustrative of the linear alkyl groups having 1–6 carbon atoms can be methyl, ethyl, propyl, butyl, pentyl and hexyl groups, and illustrative of the branched alkyl groups having 1–6 carbon atoms can be isopropyl, isobutyl and t-butyl groups.

Further, the aryl group represented by $R^6$ and $R^7$ can be a phenyl or naphthyl group. These aryl, aralkyl and heteroaralkyl groups, which are represented by $R^5$, $R^6$ and $R^7$, may each contain one or more substituent groups. Illustrative of the substituent groups can be linear or branched alkyl or alkoxyl groups having 1–6 carbon atoms, hydroxyl groups and halogen atoms. These aryl, aralkyl and heteroaryl groups may each be substituted preferably by one to three of these substituent groups. Here, examples of the linear alkyl groups having 1–6 carbon atoms can include methyl, ethyl, propyl, butyl, pentyl, and hexyl groups, and examples of the branched alkyl groups having 1–6 carbon atoms can include isopropyl, isobutyl and t-butyl groups. Illustrative of the linear alkoxyl groups having 1–6 carbon atoms can be methoxy, ethoxy, propoxy and hexyloxy groups, and illustrative of the branched alkoxyl groups having 1–6 carbon atoms can be isopropyloxy, isobutyloxy and t-butyloxy groups. Examples of the halogen atoms can include fluorine, chlorine, bromine and iodine atoms.

A hydrogen atom or ethoxycarbonyl group is particularly preferred as the group represented by $R^2$.

Among the groups which may be represented by $R^3$ and $R^4$, the alkyl group can preferably be a linear or branched alkyl group having 1–8 carbon atoms. Here, examples of the linear alkyl group having 1–8 carbon atoms can include methyl, ethyl, propyl, butyl, pentyl, hexyl, heptyl and octyl groups, and examples of the branched alkyl group having 1–8 carbon atoms can include isopropyl, isobutyl, sec-butyl and t-butyl groups. Further, the aryl group represented by $R^3$ and $R^4$ can be a phenyl or naphthyl group. The above alkyl and aryl groups may each contain one or more substituent groups. Illustrative of such substituent groups can be hydroxyl groups, alkyl groups (as substituent groups for aryl groups), alkoxyl groups, halogen atoms, piperidino groups, piperidinoalkyl(substituted)amino groups, nitroxy groups, ethoxycarbonyl groups, phenyl groups, phenylureido groups, and mercapto groups. The number of these substituent groups may preferably be from 1 to 3. Among these substituent groups, the alkyl groups can be linear or branched alkyl groups having 1–6 carbon atoms. Here, examples of the linear alkyl groups having 1–6 carbon atoms can include methyl, ethyl, propyl, butyl, pentyl and hexyl groups, while examples of the branched alkyl groups having 1–6 carbon atoms can include isopropyl, isobutyl and t-butyl groups. Further, the alkoxyl groups can preferably be those having 1–6 carbon atoms. Examples of the linear alkoxyl groups can include methoxy, ethoxy, propoxy and hexyloxy groups, while examples of the branched alkoxyl groups can include isopropyloxy, isobutyloxy and t-butyloxy groups. Illustrative of the halogen atoms can be fluorine, chlorine, bromine and iodine atoms. Examples of substituted amino groups, which may substitute on alkyl groups or aryl groups, can include amino groups substituted by one or more linear or branched $C_{1-6}$ alkyl, hydroxyalkyl, aminoalkyl, alkylaminoalkyl, aminoalkylaminoalkyl or dicyloalkyl groups, a phenylureido group, and a 2-aza-2-cyano-1-methylthiovinylamino group. Here, illustrative of the linear $C_{1-6}$ alkyl groups can be methyl, ethyl, propyl, butyl, pentyl and hexyl groups, and illustrative of the branched $C_{1-6}$ alkyl groups can be isopropyl, isobutyl and t-butyl groups.

Further, the substituted amino group represented by $R^3$ and $R^4$ can be a mono- or di-alkyl amino group. Here, each alkyl group can preferably be a linear or branched alkyl group having 1–6 carbon atoms. Examples of the linear alkyl group can include methyl, ethyl, propyl, butyl, pentyl and hexyl groups, while examples of the branched alkyl group can include isopropyl, isobutyl and t-butyl groups. A monomethylamino or dimethylamino group is preferred as the substituted amino group.

Examples of the heterocycle, which is formed by the combination of $R^3$ and $R^4$ with the adjacent nitrogen atom, can include 5-membered to 8-membered rings which may contain as hetero atoms one or more nitrogen, oxygen, sulfur and/or like atoms in addition to the adjacent nitrogen atom. Preferred examples can include piperidine ring, pyrrolidine ring, piperazine ring, and morpholine ring. Preferred examples of the groups represented by $R^3$ and $R^4$ can be a hydrogen atom as one of the groups and an alkylaminoethyl group, especially a diisopropylaminoethyl group as the other group.

Examples of the ring, which is formed by the combination of one of $R^3$ and $R^4$ with one of $R^6$ and $R^7$ in the group CON($R^6$)($R^7$), can include 5-membered to 8-membered rings, which may heterocycles containing one or more nitrogen, oxygen and/or sulfur atoms.

The substituted quinolone derivative (1) according to the present invention shall include its solvates such as its hydrate. On the other hand, no particular limitation is imposed on the salt of the substituted quinolone derivative (1) insofar as it is a pharmaceutically acceptable salt.

Examples can include inorganic acid salts such as the hydrochloride, sulfate, hydrobromide and phosphate, and organic acid salts such as the formate, acetate, fumarate, maleate and tartrate.

The substituted quinolone derivative or its salt according to the present invention can be prepared, for example, in accordance with the following Process A to Process H.

(Process A)

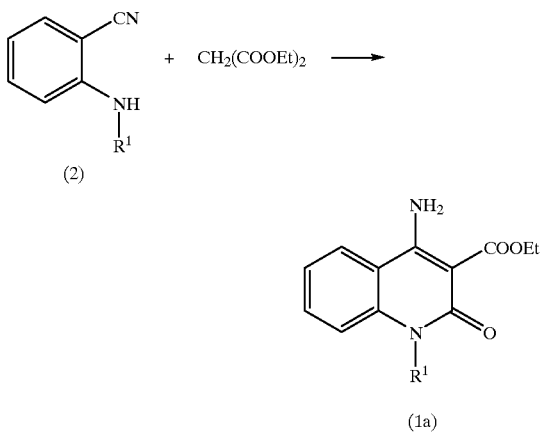

wherein $R^1$ has the same meaning as defined above.

Described specifically, the compound (2) is reacted with 1–5 equivalents, preferably 2–3 equivalents of ethyl malonate in the presence of 1–5 equivalents, preferably 2–3 equivalents of a base at 25° C. to 100° C., preferably 70° C. to 90° C. for 24 to 72 hours, whereby the compound (1a) of the present invention is obtained. This reaction can be performed under anhydrous conditions, without a solvent or in a solvent. The preferred solvent can be anhydrous ethanol, anhydrous tetrahydrofuran, anhydrous dimethylformamide or the like. The base can be sodium hydride, sodium ethoxide or the like. The compound (2) as the raw material can be synthesized in a manner known per se in the art.

(Process B)

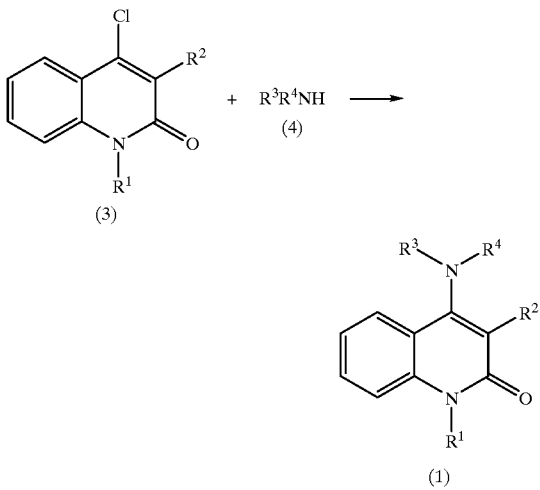

wherein $R^1$ to $R^4$ have the same meanings as defined above.

The compound (3) is reacted with 1–10 equivalents, preferably 2–3 equivalents of the amine (4) in the presence of 1–5 equivalents, preferably 2–3 equivalents of a base or in the absence of a base at 25° C. to 100° C. for 2 to 24 hours, whereby the compound (1) of the present invention is obtained. This reaction can be performed under anhydrous conditions, without a solvent or in a solvent. The preferred solvent can be anhydrous ethanol, anhydrous tetrahydrofuran, anhydrous dimethylformamide or the like. The base can be an inorganic base such as sodium hydroxide, potassium hydroxide, sodium carbonate or potassium carbonate, or an organic base such as triethylamine or dimethylaminopyridine. The compound (3) as the raw material can be synthesized in a manner known per se in the art. Further, the amine (4) is a known compound or can be synthesized in a manner known per se in the art.

If a diamine is used as the amine (4), a compound with a ring by one of $R^3$ and $R^4$ and the group $R^2$ can be obtained as the compound (1) of the present invention.

(Process C)—Preparation of Salt

A salt (1b) of the compound (1) of the present invention is obtained by reacting the compound (1) of the present invention with 1–10 equivalents, preferably 2–3 equivalents of an acid under anhydrous conditions in a solvent at 0° C. to 30° C. for 1 to 24 hours. The preferred solvent can be anhydrous methanol, anhydrous ethanol, anhydrous tetrahydrofuran, anhydrous dioxane or the like. Further, the acid can be an inorganic acid such as hydrochloric acid, sulfuric acid, hydrobromic acid or phosphoric acid, or an organic acid such as formic acid, acetic acid, fumaric acid, maleic acid or tartaric acid.

(Process D)

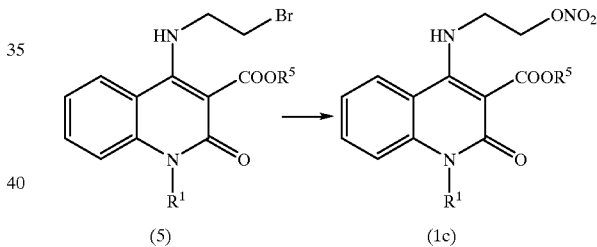

wherein $R^1$ and $R^5$ have the same meanings as defined above.

The compound (5) is reacted with 1–10 equivalents, preferably 3–5 equivalents of silver nitrate in acetonitrile at 25° C. to 100° C., preferably 70° C. to 90° C. for 5 to 10 hours, whereby the compound (1c) of the present invention is obtained. The compound (5) as the raw material can be synthesized in a manner to be described in a Referential Example.

(Process E)

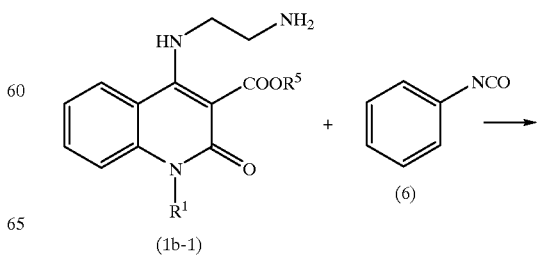

-continued

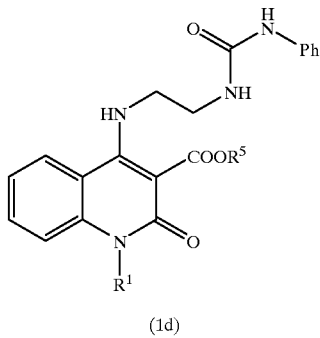

(1d)

wherein $R^1$ and $R^5$ have the same meanings as defined above.

The compound (1b-1) is reacted with 1–5 equivalents, preferably 1–2 equivalents of the phenyl isocyanate (6) under anhydrous conditions in a solvent at 50° C. to 120° C., preferably 80° C. to 100° C. for 1 to 3 hours, whereby the compound (1d) of the present invention is obtained. The preferred solvent can be anhydrous benzene, anhydrous dioxane or the like.

(Process F)

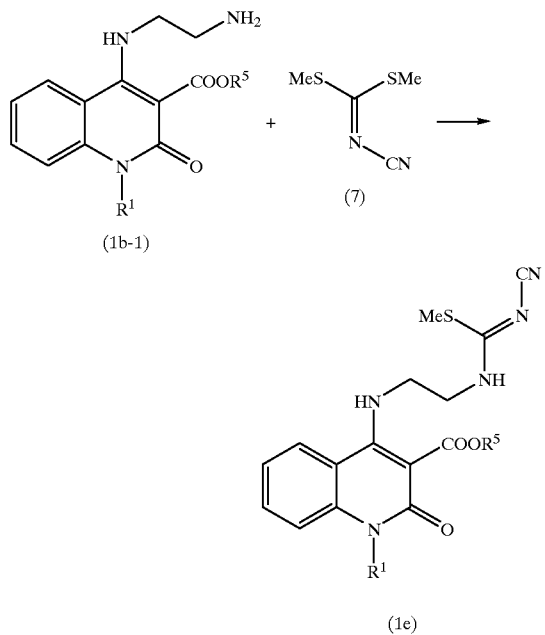

wherein $R^1$ and $R^5$ have the same meanings as defined above.

The compound (1b-1) is reacted with 1–2 equivalents of S,S'-dimethyl N-cyanodithioiminocarbonate (7) under anhydrous conditions in a solvent at 25° C. to 40° C. for 1 to 3 hours, whereby the compound (1e) of the present invention is obtained. The preferred solvent can be anhydrous methanol, anhydrous ethanol or the like.

(Process G)

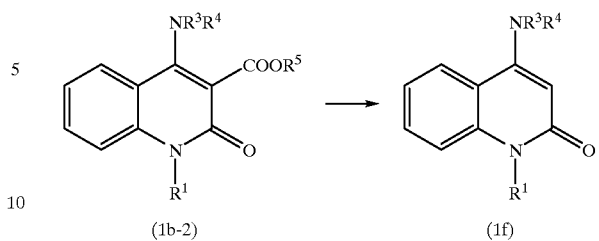

wherein $R^1$, $R^3$, $R^4$ and $R^5$ have the same meanings as defined above.

The compound (1b-2) is reacted with 3–5 equivalents of an alkali hydroxide in a solvent at 25° C. to 100° C., preferably 50° C. to 70° C. for 1 to 5 hours, whereby the compound (1f) of the present invention is obtained. The preferred solvent can be methanol, ethanol, dimethyl sulfoxide, ethylene glycol or the like. The alkali hydroxide can be sodium hydroxide, potassium hydroxide or the like.

(Process H)

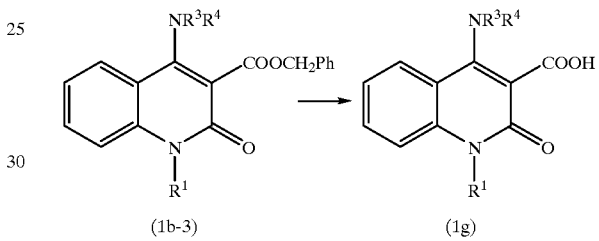

wherein $R^1$, $R^3$ and $R^4$ have the same meanings as defined above.

The compound (1b-3) is catalytically reduced in the presence of 10–50 wt. %, preferably 10–20 wt. % of 10% palladium carbon at 25° C. to 40° C. under atmospheric pressure for 1 to 7 hours, whereby the compound (1g) of the present invention is obtained. The preferred solvent can be methanol, ethanol, dimethylformamide or the like.

The compound or its salt obtained as described above can be purified further by making combined use of conventional methods such as column chromatography and recrystallization.

By a method known per se in the art, it may also be converted into a salt or solvate as needed.

The substituted quinolone derivative (1) or its salt according to the present invention has strong antiulcerative activity and therefore, is useful as a pharmaceutical such as a peptic ulcer therapeutic.

The pharmaceutical according to the present invention can be obtained by using the substituted quinolone derivative (1) or its salt and, if necessary, one or more optional ingredients commonly employed for the formulation of a dosage form and formulating them into the dosage form by a method known per se in the art. Examples of such optional ingredients can include excipients, binders, coating agents, lubricants, sugar-coating agents, disintegrators, diluents, corrigents, emulsifying, solubilizing or dispersing agents, stabilizers, pH regulators, and isotonicities.

As an administration method, oral administration is practical.

Although the preferred dose of the pharmaceutical according to the present invention varies depending on the kind and severity of the disease and the sex, age, constitution and the like of the patient, it is preferred to administer the pharmaceutical at a daily dose of from 10 to 500 mg per adult in terms of the compound (1) or its salt. This dose is administered once a day or preferably in several times a day.

The present invention will hereinafter be descried in further detail by describing working examples. It should however be borne in mind that the present invention is not limited to or by these working examples.

REFERENTIAL EXAMPLE 1

Dissolved in 30 ml of tetrahydrofuran were 0.352 g (1 mmol) of ethyl 4-(2-hydroxyethylamino)-2-oxo-1-phenyl-1, 2-dihydroquinoline-3-carboxylate, 0.67 g (2 mmol) of carbon tetrabromide and 0.531 g (2 mmol) of triphenylphosphine, followed by a reaction at room temperature for 5 hours. The insoluble matter was filtered off, and the organic layer was concentrated under reduced pressure. The resulting residue was purified by chromatography on a silica gel column and then recrystallized from ethyl acetate/isopropyl ether, whereby 0.31 g of ethyl 4-(2-bromoethylamino)-2-oxo-1-phenyl-1,2-dihydroquinoline-3-carboxylate was obtained (yield: 74.7%).

$^1$H-NMR (CDCl$_3$) δ (ppm): 7.76(1H,dd), 7.55(2H,m), 7.47(1H,t), 7.35(1H,t), 7.27(2H,m), 7.19(1H,t), 7.03(1H, br.s), 6.65(1H,dd), 4.39(2H,q), 3.90(2H,br.t), 3.65(2H,t), 1.39(3H,t).

EXAMPLE 1

Into a sodium ethoxide/ethanol solution which had been prepared from 2.07 g (90 mmol) of metallic sodium and 75 ml of anhydrous ethanol, 14.4 g (90 mmol) of ethyl malonate were added dropwise at room temperature. After the resultant mixture was stirred for 30 minutes as was, 5.82 g (30 mmol) of 2-phenylaminobenzonitrile were added and the mixture so obtained was heated under reflux for 48 hours. The reaction mixture was concentrated under reduced pressure, followed by the addition of ethyl acetate. The resulting solution was washed with water and was then dried. The solvent was distilled off under reduced pressure. The residue was purified by chromatography on a silica gel column and was then recrystallized from chloroform/hexane, whereby 4.78 g of ethyl 4-amino-2-oxo-1-phenyl-1,2-dihydro-quinoline-3-carboxylate (Compound No. 1) were obtained (yield: 51.7%).

EXAMPLES 2–6

Compounds Nos. 2–6 were obtained by conducting reactions in a similar manner as in Example 1. The structures, appearances and melting points of the compounds obtained in Examples 1–6 are shown in Table 1, and their $^1$H-NMR data are presented in Table 4.

EXAMPLE 7

Dissolved in 20 ml of tetrahydrofuran were 2.0 g (6.1 mmol) of ethyl 4-chloro-2-oxo-1-phenyl-1,2-dihydroquinoline-3-carboxylate and 8.79 g (61.0 mmol) of N,N-diisopropylethylenediamine, followed by overnight stirring at room temperature. After completion of a reaction, the solvent was distilled off under reduced pressure and the residue so obtained was added with water. The resulting mixture was extracted with chloroform, and the extract was washed with water and was then dried. The solvent was distilled off under reduced pressure. The residue was purified by chromatography on a silica gel column and was then recrystallized from isopropyl ether, whereby 2.32 g of ethyl 4-(2-diisopropylaminoethylamino)-2-oxo-1-phenyl-1,2-dihydroquinoline-3-carboxylate (Compound No. 7) were obtained (yield: 87.3%).

EXAMPLES 8–30

Compounds Nos. 8–30 were obtained by conducting reactions in a similar manner as in Example 7. The structures, appearances and melting points of the compounds obtained in Examples 7–30 are shown in Table 2, and their $^1$H-NMR data are presented in Table 5.

EXAMPLE 31

4-(2-Diisopropylaminoethylamino)-2-oxo-1-phenyl-1,2-dihydroquinoline-3-carbonitrile (Compound No. 31) was obtained in a similar manner as in Example 7 except for the use of 4-chloro-2-oxo-1-phenyl-1,2-dihydro-quinoline-3-carbonitrile instead of ethyl 4-chloro-2-oxo-1-phenyl-1,2-dihydroquinoline-3-carboxylate.

EXAMPLE 32

N3,1-Diphenyl-4-(2-diisopropylaminoethylamino)-2-oxo-1,2-dihydroquinoline-3-carboxamide (Compound No. 32) was obtained in a similar manner as in Example 7 except for the use of N3,1-diphenyl-4-chloro-2-oxo-1,2-dihydroquinoline-3-carboxamide instead of ethyl 4-chloro-2-oxo-1-phenyl-1,2-dihydroquinoline-3-carboxylate.

EXAMPLE 33

A mixture consisting of 1.0 g (3.05 mmol) of ethyl 4-chloro-2-oxo-1-phenyl-1,2-dihydroquinoline-3-carboxylate and 6.5 g (60.7 mmol) of o-toluidine was reacted at 100° C. for 5 hours. After the reaction, chloroform was added, and the resultant mixture was washed with a 5% aqueous solution of potassium hydrogensulfate and was then dried. The solvent was distilled off under reduced pressure, and the residue so obtained was purified by chromatography on a silica gel and was then recrystallized from ethanol/water, whereby 0.844 g of ethyl 4-(2-methylphenylamino)-2-oxo-1-phenyl-1,2-dihydroquinoline-3-carboxylate (Compound No. 33) was obtained (yield: 69.5%).

EXAMPLE 34

Ethyl 2-oxo-1-phenyl-4-(3-piperidylmethylphenylamino)-1,2-dihydroquinoline-3-carboxylate (Compound No. 34) was obtained in a similar manner as in Example 33 except for the use of 3-piperidylmethylaniline instead of o-toluidine.

EXAMPLE 35

Suspended in 60 ml of ethanol were 2.30 g (7 mmol) of ethyl 4-chloro-2-oxo-1-phenyl-1,2-dihydroquinoline-3-carboxylate and 2.15 g (14 mmol) of β-alanine ethyl ester hydrochloride, followed by the addition of 0.56 g (14 mmol) of sodium hydroxide. The resulting mixture was heated under reflux for 6 hours. After a reaction, the solvent was distilled off under reduced pressure and the residue so obtained was added with ethyl acetate. The resulting solution was washed with water and was then dried. The solvent was distilled off under reduced pressure. The residue so obtained was purified by chromatography on a silica gel column and was then recrystallized from ethyl acetate/isopropyl ether, whereby 2.08 g of ethyl 3-(3-ethoxycarbonyl-2-oxo-1-phenyl-4-(1,2-dihydroquinolyl)-amino)propanoate (Compound No. 35) were obtained (yield: 72.8%).

EXAMPLE 36

Ethyl 4-chloro-2-oxo-1-phenyl-1,2-dihydroquinoline-3-carboxylate (4.0 g, 9.2 mmol) was dissolved in 40 ml of tetrahydrofuran, followed by the addition of 14.64 g (244 mmol) of ethylenediamine. The resulting mixture was stirred overnight at room temperature and was then heated under reflux for 5 hours. The solvent was distilled off under reduced pressure, and the residue so obtained was added with chloroform. Precipitated crystals were collected by filtration and were then recrystallized from ethanol, whereby 1.33 g of 7-phenyl-2,3,4,5,6,7-hexahydro-1-benzo[5,6]azino-[4,3-e][1,4]diazepine-5,6-dione (Compound No. 36) were obtained (yield: 35.7%).

EXAMPLE 37

In 30 ml of anhydrous dioxane, 2.18 g (5 mmol) of ethyl 4-(2-diisopropylaminoethylamino)-2-oxo-1-phenyl-1,2-dihydroquinolinecarboxylate (Compound No. 7) were dissolved, followed by the addition of 2 ml of 4N-hydrochloric acid/dioxane solution. The resulting mixture was reacted at room temperature for 4 hours. Precipitated white powder was collected by filtration and was then washed with diethyl ether, whereby 1.06 g of ethyl 4-(2-diisopropylaminoethylamino)-2-oxo-1-phenyl-1,2-dihydroquinolinecarboxylate hydrochloride (Compound No. 37) were obtained (yield: 44.9%).

EXAMPLE 38

Ethyl 4-(2-(2-diethylaminoethylisopropylamino)-ethylamino)-2-oxo-1-phenyl-1,2-dihydroquinoline-3-carboxylate hydrochloride (Compound No. 38) was obtained in a similar manner as in Example 37 except for the use of ethyl 4-(2-(2-diethylaminoethylisopropylamino)ethylamino)-2-oxo-1-phenyl-1,2-dihydroquinoline-3-carboxylate (Compound No. 28) instead of ethyl 4-(2-diisopropylaminoethylamino)-2-oxo-1-phenyl-1,2-dihydroquinolinecarboxylate (Compound No. 7).

EXAMPLE 39

Dissolved in 30 ml of acetonitrile was 0.83 g (2 mmol) of the ethyl 4-(2-bromoethylamino)-2-oxo-1-phenyl-1,2-dihydroquinoline-3-carboxylate obtained in Referential Example 1, followed by the addition of 1.7 g (10 mmol) of silver nitrate. The resulting mixture was then heated under reflux for 7 hours. An aqueous solution of sodium chloride was added to consume up excess silver nitrate. The reaction mixture was filtered through Celite (trade mark), and the filtrate was concentrated under reduced pressure. The residue so obtained was added with ethyl acetate. The resulting solution was washed with water and was then dried. The solvent was distilled off under reduced pressure, and the residue so obtained was purified by chromatography on a silica gel and was then recrystallized from ethyl acetate/isopropyl ether, whereby 0.75 g of ethyl 4-(2-nitroxyethylamino)-2-oxo-1-phenyl-1,2-dihydroquinoline-3-carboxylate (Compound No. 39) was obtained (yield: 94.5%).

EXAMPLE 40

Dissolved in 10 ml of anhydrous dioxane was 0.8 g (1.8 mmol) of ethyl 4-(2-aminoethylamino)-2-oxo-1-phenyl-1,2-dihydroquinoline-3-carboxylate (Compound No. 15), followed by the addition of 0.221 g (1.9 mmol) of phenyl isocyanate. The resulting mixture was heated under reflux for 1 hour. After the reaction mixture was allowed to cool down, the reaction mixture was diluted with diethyl ether. The resulting precipitate was collected by filtration and was then dried, whereby 0.78 g of ethyl 2-oxo-1-phenyl-4-(2-phenylaminocarbonylaminoethylamino)-1,2-dihydroquinoline-3-carboxylate (Compound No. 40) was obtained (yield: 73.0%).

EXAMPLE 41

Suspended in 20 ml of anhydrous benzene were 1.40 g (3.8 mmol) of N3-(2-aminoethyl)-4-(2-aminoethylamino)-2-oxo-1-phenyl-1,2-dihydroquinoline-3-carboxamide, followed by the addition of 0.87 ml (8.1 mmol) of phenyl isocyanate. The resuling mixture was then heated under reflux for 2 hours. After the reaction mixture was allowed to cool down, the reaction mixture was diluted with diethyl ether. The resulting precipitate was collected by filtration and was then dried, whereby 1.39 g of 2-oxo-1-phenyl-4-(2-phenylaminocarbonylaminoethylamino)-3-(1,2-dihydroquinolyl)-N-(2-phenylaminocarbonylaminoethyl)formamide (Compound No. 41) were obtained (yield: 60.0%).

EXAMPLE 42

In 15 ml of anhydrous ethanol, 1.30 g (2.9 mmol) of ethyl 4-(2-aminoethylamino)-2-oxo-1-phenyl-1,2-dihydroquinoline-3-carboxylate (Compound No. 15) and 0.47 g (2.9 mmol) of S,S'-dimethyl N-cyanodithioiminocarbonate were reacted at room temperature for 1 hour. The solvent was distilled off under reduced pressure, and the residue so obtained was purified by chromatography on a silica gel column, whereby 0.86 g of ethyl 4-(2-(2-aza-2-cyano-1-methylthiovinylamino)ethyl)amino-2-oxo-1-phenyl-1,2-dihydroquinoline-3-carboxylate (Compound No. 42) was obtained (yield: 52.0%).

EXAMPLE 43

Dissolved in 50 ml of dimethylsulfoxide were 1.31 g (3 mmol) of ethyl 4-(2-diisopropylaminoethylamino)-2-oxo-1-phenyl-1,2-dihydroquinoline-3-carboxylate (Compound No. 7), followed by the addition of a solution of 0.68 g (10 mmol) of potassium hydroxide in 6 ml of water. They were reacted at 60° C. for 4 hours. The reaction mixture was poured into ice water, and the resulting precipitate was collected by filtration, washed with water and then dried. The resulting powder was dissolved in chloroform, purified by chromatography on a silica gel column, and then recrystallized from isopropyl ether, whereby 0.78 g of 4-(2-diisopropylaminoethylamino)-1-phenyl-1,2-dihydroquinolin-2-one (Compound No. 43) was obtained (yield: 71.6%).

EXAMPLE 44

Dissolved in 150 ml of methanol were 1.50 g (3 mmol) of benzyl 4-(2-diisopropylaminoethylamino)-2-oxo-1-phenyl-1,2-dihydroquinoline-3-carboxylate (Compound No. 20), followed by the addition of 0.8 g of 10% palladium carbon. Catalytic reduction was then conducted at room temperature and atmospheric pressure for 6 hours. The catalyst was filtered off and the filtrate was concentrated under reduced pressure. The residue so obtained was recrystallized from methanol/isopropyl ether, whereby 0.95 g of 4-(2-diisopropylaminoethylamino)-2-oxo-1-phenyl-1,2-dihydroquinoline-3-carboxylic acid (Compound No. 44) was obtained (yield: 77.8%).

The structures, appearances and melting points of the compounds obtained in Examples 31–44 are shown in Table 3, and their $^1$H-NMR data are presented in Table 6.

TABLE 1
| Compound No. | R¹ | R² | R³ | R⁴ | Appearance | Melting point (°C.) |
|---|---|---|---|---|---|---|
| 1 | 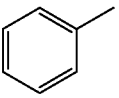 | COOEt | H | H | White crystals | 235–237 (decomp) |
| 2 | 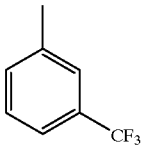 | COOEt | H | H | White crystals | 209–210 (decomp) |
| 3 | 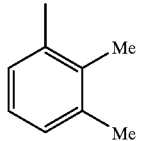 | COOEt | H | H | White crystals | 240–242 (decomp) |
| 4 | 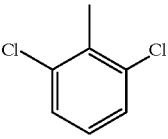 | COOEt | H | H | White crystals | 218–220 (decomp) |
| 5 | 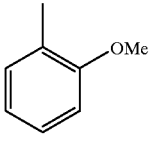 | COOEt | H | H | White crystals | 228–230 (decomp) |
| 6 | 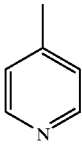 | COOEt | H | H | White crystals | 240–242 (decomp) |

TABLE 2

| Compound No. | $R^1$ | $R^2$ | $R^3$ | $R^4$ | Appearance | Melting point (° C.) |
|---|---|---|---|---|---|---|
| 7 | Ph | COOEt | H | $CH_2CH_2N(i-Pr)_2$ | White crystals | 172–174 (decomp) |
| 8 | Ph | COOEt | H | Me | White crystals | 220–221 (decomp) |
| 9 | Ph | COOEt | H | Et | White crystals | 188–189 (decomp) |
| 10 | Ph | COOEt | Me | Me | White crystals | 130–131 |
| 11 | Ph | COOEt | H | $n-C_6H_{13}$ | White crystals | 122–123 |
| 12 | Ph | COOEt | H | $CH_2Ph$ | White crystals | 169–170 (decomp) |
| 13 | Ph | COOEt | H | $CH_2CH_2OH$ | White crystals | 179–180 (decomp) |
| 14 | Ph | COOEt | |  | White crystals | 212–214 (decomp) |
| 15 | Ph | COOEt | H | $CH_2CH_2NH_2$ | Amorphous powder | 95–97 (decomp) |
| 16 | Ph | COOEt | H | $CH_2CH_2NHMe$ | Syrup | |
| 17 | Ph | COOEt | H | Ph | Amorphous powder | 146–147 (decomp) |
| 18 | Ph | COOEt | H | $CH_2CH_2NH-n-C_4H_9$ | Syrup | |
| 19 | Ph | COOEt | H | $(CH_2)_2NH(CH_2)_2OH$ | Syrup | |
| 20 | Ph | $COOCH_2Ph$ | H | $CH_2CH_2N(i-Pr)_2$ | Syrup | |
| 21 | Ph | COOEt | H | $CH_2CH_2SH$ | Amorphous powder | 117–119 (decomp) |
| 22 | Ph | COOEt | H | $NMe_2$ | White crystals | 128–129 |
| 23 | Ph | COOEt | H | $(CH_2)_8-NH_2$ | Syrup | |
| 24 | Ph | COOEt | H | 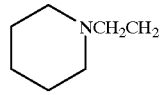 | Syrup | |
| 25 | Ph | COOEt | H | $(CH_2)_2NH(CH_2)_2NH_2$ | Syrup | |
| 26 | Ph | COOEt | H | $(CH_2)_3NH(CH_2)_4NH(CH_2)_3NH_2$ | Syrup | |
| 27 | Ph | COOEt | H | 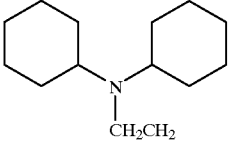 | White crystals | 177–179 (decomp) |
| 28 | Ph | COOEt | H | $(CH_2)_2N(i-Pr)(CH_2)_2NEt_2$ | Syrup | |
| 29 | Ph | COOEt | | 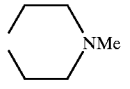 | White crystals | 214–216 (decomp) |
| 30 | Ph | COOEt | |  | White crystals | 185–188 (decomp) |

TABLE 3

| Compound No. | R¹ | R² | R³ | R⁴ | Appearance | Melting point (° C.) |
|---|---|---|---|---|---|---|
| 31 | Ph | CN | H | CH₂CH₂N(i-Pr)₂ | White crystals | 193–195 (decomp) |
| 32 | Ph | CONHPh | H | CH₂CH₂N(i-Pr)₂ | White crystals | 122–124 |
| 33 | Ph | COOEt | H | 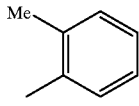 | White crystals | 185–186 (decomp) |
| 34 | Ph | COOEt | H | 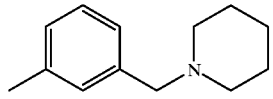 | White crystals | 95–97 |
| 35 | Ph | COOEt | H | CH₂CH₂COOEt | White crystals | 143–144 |
| 36 | Ph | CONHCH₂CH₂ | H | H | White crystals | 214–216 (decomp) |
| 37 | Ph | COOEt | H | CH₂CH₂N(i-Pr)₂.HCl | White crystals | 200–203 (decomp) |
| 38 | Ph | COOEt | H | (CH₂)₂N(i-Pr) (CH₂)₂NEt₂.2HCl | White crystals | 202–204 (decomp) |
| 39 | Ph | COOEt | H | CH₂CH₂ONO₂ | White crystals | 157–158 (decomp) |
| 40 | Ph | COOEt | H | CH₂CH₂NHCONHPh | White crystals | 218–220 (decomp) |
| 41 | Ph | 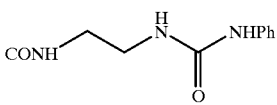 | H | CH₂CH₂NHCONHPh | White crystals | 207–209 (decomp) |
| 42 | Ph | COOEt | H | 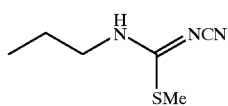 | White crystals | 204–206 (decomp) |
| 43 | Ph | H | H | CH₂CH₂N(i-Pr)₂ | White crystals | 142–143 |
| 44 | Ph | COOH | H | CH₂CH₂N(i-Pr)₂ | White crystals | 164–165 (decomp) |

TABLE 4

| Comp'd No. | δ: ppm in CDCl₃ |
|---|---|
| 1 | 7.80(2H,br.), 7.71(1H,dd), 7.50–7.55(2H,m), 7.40–7.50(1H,m), 7.35(1H,ddd), 7.20–7.30(2H,m), 7.12(1H,ddd), 6.56(1H,dd), 4.37(2H,q), 1.38(3H,t) |
| 2 | 7.90(2H,br.), 7.65–7.75(3H,m), 7.55(1H,s), 7.45–7.50(1H,m), 7.39(1H,ddd), 7.17(1H,dd), 6.50(1H,dd), 4.39(2H,q), 1.39(3H,t) |
| 3 | 6.88–7.80(6H,m), 6.52(1H,dd), 4.40(2H,q), 2.32(3H,s), 1.88(3H,s), 1.40(3H,t) |
| 4 | 7.90(2H,br.), 7.71(1H,dd), 7.50(2H,d), 7.44(1H,ddd), 7.36(1H,dd), 7.23(1H,ddd), 6.45 (1H,dd), 4.39(2H,q), 1.39(3H,t) |
| 5 | 7.65(2H,br.), 7.63(1H,dd), 7.44(1H,ddd), 7.37(1H,ddd), 7.05–7.25(4H,m), 6.57(1H,dd), 4.38(2H,q), 3.70(3H,s), 1.39(3H,t) |
| 6 | 8.83(2H,dd), 7.90(2H,br.), 7.72(1H,dd), 7.42(1H,ddd), 7.27(2H,dd), 7.22(1H,ddd), 6.55(1H,dd), 4.39(2H,q), 1.39(3H,t) |

TABLE 5

| Comp'd No. | δ: ppm in CDCl₃ |
|---|---|
| 7 | 7.68(1H,dd), 7.50–7.60(2H,m), 7.45–7.50(1H,m), 7.20–7.35(3H,m), 7.10–7.20(1H,m), 6.92(1H,br.t), |

TABLE 5-continued

| Comp'd No. | δ: ppm in CDCl₃ |
|---|---|
|  | 6.64(1H,dd), 4.38(2H,q), 3.32(2H,td), 3.14(2H,sept.), 2.83(2H,t), 1.39(3H,t), 1.10 (12H,d) |
| 8 | 7.79(1H,dd), 7.50–7.60(2H,m), 7.35–7.50(2H,m), 7.31(1H,ddd), 7.20–7.30(2H,m), 7.12(1H,ddd), 6.62(1H,dd), 4.37(2H,q), 3.22(3H,s), 1.38(3H,t) |
| 9 | 7.81(1H,dd), 7.50–7.60(3H,m), 7.40–7.50(1H,m), 7.32(1H,ddd), 7.20–7.30(2H,m), 7.13(1H,ddd), 6.61(1H,dd), 4.37(2H,q), 3.64(2H,q), 1.41(3H,t), 1.39(3H,t) |
| 10 | 7.91(1H,dd), 7.50–7.60(2H,m), 7.45–7.50(1H,m), 7.25–7.35(3H,m), 7.18(1H,ddd), 6.66(1H,dd), 4.40(2H,q), 3.05(6H,s), 1.39(3H,t) |
| 11 | 7.82(1H,dd), 7.80(1H,br.), 7.50–7.60(2H,m), 7.40–7.50(1H,m), 7.31(1H,ddd), 7.20–7.30(2H,m), 7.13(1H,ddd), 6.60(1H,dd), 4.37(2H,q), 3.59(2H,t), 1.76(2H,quint.), 1.30–1.50(6H,m), 1.38(3H,t), 0.91(3H,t) |
| 12 | 7.71(1H,dd), 7.50–7.60(2H,m), 7.20–7.50(10H,m), 7.10(1H,ddd), 6.64(1H,dd), 4.71(2H,s), 4.35(2H,q), 1.35(3H,t) |
| 13 | 7.84(1H,dd), 7.50–7.60(2H,m), 7.40–7.50(1H,m), 7.31(1H,ddd), 7.20–7.30(3H,m), 7.14(1H,ddd), 6.62(1H,dd), 4.36(2H,q), 3.84(2H,t), 3.61(2H,br.t), |

TABLE 5-continued

| Comp'd No. | δ: ppm in CDCl₃ |
|---|---|
| | 2.60(1H,br.), 1.36(3H,t) |
| 14 | 7.94(1H,dd), 7.50–7.60(2H,m), 7.45–7.50(1H,m), 7.34(1H,ddd), 7.25–7.35(2H,m), 7.20–7.25(1H,m), 6.69(1H,dd), 4.42(2H,q), 3.94(2H,t), 3.32(2H,t), 1.40(3H,t) |
| 15 | 7.86(1H,dd), 7.50–7.60(3H,m), 7.40–7.50(1H,m), 7.20–7.30(3H,m), 7.10–7.20(1H,m), 6.60(1H,dd), 4.35(2H,q), 3.52(2H,td), 3.08(2H,t), 2.26(2H,br.), 1.36(3H,t) |
| 16 | 7.85(1H,dd), 7.50–7.60(2H,m), 7.40–7.50(1H,m), 7.20–7.35(4H,m), 7.15–7.20(1H,m), 6.62(1H,dd), 4.36(2H,q), 3.51(2H,td), 2.97(2H,t), 2.55(1H,br.), 2.50(3H,s), 1.37(3H,t) |
| 17 | 10.0(1H,s), 7.55–7.65(3H,m), 7.45–7.55(1H,m), 7.25–7.35(5H,m), 7.05–7.15(3H,m), 6.85–6.90(1H,m), 6.60(1H,dd), 4.33(2H,q), 1.36(3H,t) |
| 18 | 7.76(1H,dd), 7.50–7.60(2H,m), 7.40–7.50(1H,m), 7.20–7.35(4H,m), 7.15–7.20(1H,m), 6.62(1H,dd), 4.37(2H,q), 3.46(2H,td), 2.97(2H,t), 2.67(2H,t), 1.70(1H,br.), 1.51(2H,quint.), 1.38(3H,t), 1.35–1.45(4H,m), 0.94(3H,t) |
| 19 | 8.14(1H,br.t), 7.83(1H,dd), 7.50–7.60(2H,m), 7.45–7.50(1H,m), 7.20–7.35(3H,m), 7.10–7.20(1H,m), 6.60(1H,dd), 4.37(2H,q), 3.70(2H,t), 3.61(2H,td), 2.98(2H,t), 2.85(2H,t), 2.20(2H,br.), 1.38(3H,t) |
| 20 | 7.62(1H,dd), 7.45–7.55(5H,m), 7.25–7.40(6H,m), 7.15(1H,m), 6.79(1H,br.t), 6.63(1H,dd), 5.36(2H,s), 3.00–3.10(4H,m), 2.59(2H,t), 1.04(12H,d) |
| 21 | 7.79(1H,dd), 7.40–7.60(3H,m), 7.41(1H,br.t), 7.30–7.40(1H,m), 7.20–7.30(2H,m), 7.10–7.20(1H,m), 6.63(1H,dd), 4.38(2H,q), 3.70(2H,td), 2.88(2H,td), 1.53(1H,t), 1.39(3H,t) |
| 22 | 7.91(1H,dd), 7.50–7.60(2H,m), 7.45–7.50(1H,m), 7.20–7.35(3H,m), 7.15–7.20(1H,m), 6.65(1H,dd), 4.41(2H,q), 3.05(6H,s), 1.39(3H,t) |
| 23 | 7.82(1H,dd), 7.78(1H,br.t), 7.50–7.60(2H,m), 7.40–7.50(1H,m), 7.20–7.35(3H,m), 7.13(1H,ddd), 6.60(1H,dd), 4.37(2H,q), 3.58(2H,td), 2.68(2H,t), 1.75(2H,quint.), 1.25–1.55(12H,m), 1.38(3H,t) |
| 24 | 7.65–7.75(1H,m), 7.50–7.60(2H,m), 7.45–7.50(1H,m), 7.20–7.35(3H,m), 7.15–7.20(1H,m), 7.03(1H,br.), 6.64(1H,dd), 4.37(2H,q), 3.41(2H,td), 2.66(2H,t), 2.40–2.60(4H,m), 1.40–1.80(6H,m), 1.39(3H,t) |
| 25 | 7.79(1H,dd), 7.00–7.70(8H,m), 6.62(1H,dd), 4.37(2H,q), 3.35–3.70(2H,m), 2.55–3.15(6H,m), 1.50(3H,br.s), 1.38(3H,t) |
| 26 | 8.56(1H,br.t), 7.84(1H,dd), 7.50–7.55(2H,m), 7.40–7.50(1H,m), 7.25–7.35(3H,m), 7.10(1H,ddd), 6.61(1H,dd), 4.36(2H,q), 3.55(2H,td), 2.92(2H,t), 2.76(2H,t), 2.60–2.75(6H,m), 1.84(2H,quint.), 1.50–1.70(6H,m), 1.38(3H,t), 1.36(4H,br.) |
| 27 | 7.68(1H,dd), 7.50–7.60(2H,m), 7.40–7.50(1H,m), 7.20–7.35(3H,m), 7.16(1H,ddd), 6.95(1H,br.t), 6.64(1H,dd), 4.38(2H,q), 3.30(2H,td), 2.91(2H,t), 2.55–2.65(2H,m), 1.70–1.85(8H,m), 1.60–1.70(2H,m), 1.40(3H,t), 1.20–1.40(8H,m), 1.00–1.15(2H,m) |
| 28 | 7.80(1H,dd), 7.50–7.60(2H,m), 7.40–7.50(1H,m), 7.25–7.35(3H,m), 7.15(1H,ddd), 7.10(1H,br.t), 6.63(1H,dd), 4.37(2H,q), 3.36(2H,td), 3.04(1H,sept.), 2.77(2H,t), 2.50–2.65(8H,m), 1.39(3H,t), 1.06(6H,d), 1.02(6H,t) |
| 29 | 7.92(1H,dd), 7.45–7.60(3H,m), 7.33(1H,ddd), 7.25–7.30(2H,m), 7.19(1H,ddd), 6.67(1H,dd), 4.40(2H,q), 3.34(4H,t), 2.60–2.80(4H,m), 2.41(3H,s), 1.39(3H,t) |
| 30 | 7.95(1H,dd), 7.45–7.60(3H,m), 7.33(1H,ddd), 7.25–7.30(2H,m), 7.20(1H,ddd), 6.67(1H,dd), 4.41(2H,q), 3.25–3.35(4H,m), 3.05–3.15(4H,m), 1.40(3H,t) |

TABLE 6

| Comp'd No. | δ: ppm in CDCl₃ (unless otherwise specifically indicated by *) |
|---|---|
| 31 | 7.63(1H,d), 7.45–7.60(3H,m), 7.40(1H,br.), 7.37(1H,ddd), 7.15–7.25(3H,m), 6.65(1H,dd), 3.99(2H,td), 3.17(2H,sept.), 2.90(2H,t), 1.12(12H,d) |
| 32 | 12.6(1H,s), 11.7(1H,br.s), 8.16(1H,dd), 7.60–7.70(4H,m), 7.54(1H,ddd), 7.25–7.40(5H,m), 7.16(1H,ddd), 7.00–7.05(1H,m), 6.60(1H,dd), 3.81(2H,td), 3.07(2H,sept.), 2.82(2H,t), 1.05(12H,d) |
| 33 | 10.3(1H,s), 7.40–7.60(4H,m), 7.20–7.35(4H,m), 7.05–7.15(2H,m), 6.80–6.90(2H,m), 6.59(1H,dd), 4.32(2H,q), 2.45(3H,s), 1.37(3H,t) |
| 34 | 10.1(1H,s), 6.40–7.80(13H,m), 4.33(2H,q), 3.40(2H,s), 2.30(4H,br.s), 1.10–1.80(9H,m) |
| 35 | 7.74(1H,dd), 7.50–7.60(2H,m), 7.40–7.50(1H,m), 7.32(1H,ddd), 7.20–7.30(2H,m), 7.15–7.20(2H,m), 6.63(1H,dd), 4.37(2H,q), 4.21(2H,q), 3.75(2H,td), 2.73(2H,t), 1.39(3H,t), 1.29(3H,t) |
| 36* | 8.03(1H,dd), 7.78(1H,t), 7.50–7.60(2H,m), 7.45–7.50(1H,m), 7.25–7.40(2H,m), 7.20–7.25(2H,m), 7.15(1H,ddd), 6.42(1H,dd), 3.55–3.65(2H,m), 3.40–3.50(2H,m) |
| 37* | 10.2(1H,br.s), 8.48(1H,dd), 7.74(1H,br.t), 7.50–7.60(2H,m), 7.42(1H,ddd), 7.20–7.30(3H,m), 6.50(1H,dd), 4.28(2H,q), 3.60–3.75(4H,m), 3.30–3.40(2H,m), 1.36(6H,d), 1.31(6H,d), 1.29(3H,t) |
| 38* | 11.3(1H,br.s), 11.2(1H,br.s), 8.40–8.50(1H,m), 7.50–7.65(4H,m), 7.40–7.45(1H,m), 7.20–7.30(3H,m), 6.50(1H,dd), 4.30(2H,q), 3.10–3.80(13H,m), 1.20–1.40(15H,m) |
| 39 | 7.72(1H,dd), 7.50–7.60(2H,m), 7.45–7.50(1H,m), 7.36(1H,ddd), 7.25–7.30(2H,m), 7.18(1H,ddd), 7.05(1H,br.t), 6.65(1H,dd), 4.71(2H,t), 4.38(2H,q), 3.87(2H,td), 1.39(3H,t) |
| 40* | 8.67(1H,s), 8.17(1H,d), 7.30–7.70(6H,m), 7.15–7.30(6H,m), 6.91(1H,tr), 6.40–6.55(2H,m), 4.22(2H,q), 3.40–3.55(2H,m), 3.30–3.40(2H,m), 1.27(3H,t) |
| 41* | 10.9(1H,br.), 10.1(1H,br.t), 8.62(1H,s), 8.44(1H,s), 8.17(1H,d), 7.15–7.65(15H,m), 6.80–6.95(2H,m), 6.46–6.49(1H,m), 6.40(1H,t), 6.24(1H,t), 3.75–3.85(2H,m), 3.40–3.50(2H,m), 3.30–3.40(2H,m), 3.20–3.30(2H,m) |
| 42** | 7.10–8.00(8H,m), 6.50–6.80(1H,m), 4.30(2H,q), 3.40–3.90(4H,m), 2.48(3H,s), 1.32(3H,t) |
| 43 | 7.40–7.60(4H,m), 7.20–7.30(3H,m), |

TABLE 6-continued

| Comp'd No. | δ: ppm in CDCl$_3$ (unless otherwise specifically indicated by *) |
|---|---|
|  | 7.15(1H,ddd), 6.63(1H,dd), 6.08(1H,br.t), 5.74(1H,s), 3.18(2H,br.q), 3.11(2H,sept.), 2.89(2H,t), 1.10(12H,d) |
| 44 | 15.8(1H,s), 11.4(1H,br.s), 8.24(1H,dd), 7.50–7.65(3H,m), 7.43(1H,ddd), 7.20–7.30(3H,m), 6.71(1H,dd), 3.90(2H,td), 3.11(2H,sept.), 2.85(2H,t), 1.07(12H,d) |

*in DMSO-d$_6$
**in CDCl$_3$ + CD$_3$OD

Test 1

Anti-ulcer Test with An Ulcer Model Induced by Water-immersed Restraint Stress in Rats SD male rats (180 to 210 g) fasted for 24 hours were used with 8 rats per group. The rats were orally administered with test compounds. Immediately after that, the rats were placed in a restraint cage (the University of Tokyo type). After the rats were immersed to the level of the xiphoid process in a water bath (21° C.) for 7 hours to apply stress, they were pulled out of the water bath and killed by ether anesthesia. The stomach of each rat was removed and inflated with 10 ml of 2% formalin. Further, the stomach was immersed in the same solution for light fixation. The stomach was opened along the greater curvature. The ulcer index was determined as the sum of the lengths (mm) of ulcers on the gastric glandular portion per rat under a dissecting microscope (×10 magnification).

Cimetidine was used as a positive control drug.

Further, the percent (%) inhibition was calculated in accordance with the following formula:

$$100 - \left[ \frac{\text{Ulcer index of a group administered with test compound}}{\text{Ulcer index of control group}} \right] \times 100 = \text{Percent (\%) inhibition}$$

TABLE 7

| Test Compound | Dose (mg/kg p.o.) | Ulcer index (mm)* | Percent (%) inhibition |
|---|---|---|---|
| Compound No. 7 | 100 | 4.5 ± 1 | 79.6 |
| Compound No. 28 | 100 | 1.4 ± 1 | 93.7 |
| Compound No. 31 | 100 | 2.5 ± 1 | 88.7 |
| Compound No. 43 | 100 | 0.5 ± 0 | 97.7 |
| Compound No. 44 | 100 | 3.4 ± 1 | 84.6 |
| Control group | — | 22.1 ± 5 |  |
| Cimetidine | 100 | 9.8 ± 3 | 55.7 |

*Each ulcer index is indicated by a mean ± S.E.

We claim:

1. A substituted quinolone derivative represented by the following formula (1) or a salt thereof:

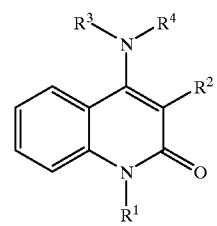

(1)

wherein
R$^1$ represents a substituted or unsubstituted aryl, pyridyl or pyrimidyl group,
R$^2$ represents a group COOR$^5$, a group CON(R$^6$)R$^7$, or a cyano group;
in which R$^2$ radical:
R$^5$ represents a hydrogen atom or a substituted or unsubstituted alkyl, aralkyl or heteroaralkyl group,
R$^6$ and R$^7$ may by the same or different and each independently represent a hydrogen atom or a substituted or unsubstituted alkyl or aryl group;
R$^3$ and R$^4$ may be the same or different and each independently represent a hydrogen atom or a substituted or unsubstituted alkyl, aryl or amino group; or
R$^3$ and R$^4$ are combined with the adjacent nitrogen atom to form a heterocycle;
or one of R$^3$ and R$^4$ and one of R$^6$ and R$^7$ are combined together to form a ring.

2. A substituted quinolone derivative of formula (1) or a salt thereof according to claim 1, wherein R$^1$ represents a phenyl group, R$^2$ represents an ethoxycarbonyl group and R$^3$ represents a hydrogen atom.

3. A pharmaceutical composition comprising as an active ingredient a substituted quinolone derivative or a salt thereof as defined in claim 1.

4. A method for therapeutically treating peptic ulcer in a subject, comprising administering to said subject a therapeutically effective amount for treating peptic ulcer of a substituted quinolone derivative represented by the following formula (1) or a salt thereof:

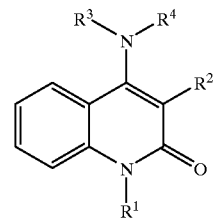

(1)

wherein
R$^1$ represents a substituted or unsubstituted aryl, pyridyl or pyrimidyl group,
R$^2$ represents a hydrogen atom, a group COOR$^5$, a group CON(R$^6$)R$^7$, or a cyano group;
in which R$^2$ is radical:
R$^5$ represents a hydrogen atom or a substituted or unsubstituted alkyl, aralkyl or heteroaralkyl group,
R$^6$ and R$^7$ may by the same or different and each independently represent a hydrogen atom or a substituted or unsubstituted alkyl or aryl group;

$R^3$ and $R^4$ may be the same or different and each independently represent a hydrogen atom or a substituted or unsubstituted alkyl, aryl or amino group; or $R^3$ and $R^4$ are combined with the adjacent nitrogen atom to form a heterocycle;

or one of $R^3$ and $R^4$ and one of $R^6$ and $R^7$ are combined together to form a ring.

5. The method for therapeutically treating peptic ulcer in a subject according to claim 4, wherein in the substituted quinolone derivative of the formula (1) or a salt thereof $R^1$ represents a phenyl group, $R^2$ represents an ethoxycarboxyl group and $R^3$ represents a hydrogen atom.

* * * * *